United States Patent [19]

Fenton

[11] Patent Number: 4,911,699
[45] Date of Patent: Mar. 27, 1990

[54] DEODORIZING OSTOMY POUCH

[75] Inventor: Leonard Fenton, Beachwood, Ohio

[73] Assignee: Marlen Manufacturing & Development Co., Bedford, Ohio

[21] Appl. No.: 230,464

[22] Filed: Aug. 10, 1988

Related U.S. Application Data

[63] Continuation of Ser. No. 25,994, Mar. 16, 1987, abandoned.

[51] Int. Cl.$^4$ ............................................. A61F 5/44
[52] U.S. Cl. .................................................. 604/333
[58] Field of Search ......................... 604/333, 359, 325; 55/385.4, 387

[56] References Cited

U.S. PATENT DOCUMENTS

| | | | |
|---|---|---|---|
| 3,312,221 | 4/1967 | Overment | 604/333 |
| 4,211,224 | 7/1980 | Kubach et al. | 604/333 |
| 4,367,742 | 1/1983 | Ornstein | 604/333 |
| 4,372,308 | 2/1983 | Steer et al. | 604/333 |
| 4,411,659 | 10/1983 | Jensen et al. | 604/333 |

FOREIGN PATENT DOCUMENTS

| | | | |
|---|---|---|---|
| 0068964 | 1/1983 | European Pat. Off. | 604/333 |
| 2149306 | 6/1985 | United Kingdom | 604/333 |

Primary Examiner—Jerome L. Kruter
Attorney, Agent, or Firm—Pearne, Gordon, McCoy & Granger

[57] ABSTRACT

A deodorizing ostomy drainage receptacle comprising a flexible pouch having drainage chamber defining walls therein and an opening in one of the walls. The opening is located in an upper portion of the pouch and is capable of receiving a stoma. An aperture is also desirably located in the upper portion of the pouch and permits gas to egress therefrom. A deodorant is attached to the upper portion of the pouch in the vicinity of the aperture and is contained in a separate bag so that the gas must pass through the deodorant before egressing from the pouch. The deodorant is generally a solid material such as activated charcoal.

6 Claims, 1 Drawing Sheet

DEODORIZING OSTOMY POUCH

This is a continuation of application Ser. No. 025,994 filed Nov. 16, 1987, now abandoned.

FIELD OF THE INVENTION

This invention relates to ostomy drainage receptacles and, more particularly, to ostomy appliances comprising a flexible pouch for receiving discharge from the stoma of a patient and having a deodorant attached to the pouch to substantially abate odor egressing therefrom.

BACKGROUND OF THE INVENTION

In the art of ostomy appliances, some effort has been devoted to suppressing, abating, or eliminating the often offensive odors which accompany the use of the appliance. Such odor is generally socially offensive and thus acts as a deterrent to individuals from engaging in normal social activities. Although numerous ostomy drainage receptacles are known and have a stoma receiving opening therein, they do not generally relate to suppressing, abating, etc. odors emanating therefrom. Examples of such appliances include U.S. Pat. Nos. 2,784,718; 2,595,934; 2,684,676; 3,897,780; 4,219,023; and Reissue No. 29,453.

A particular prior art device is shown in FIG. 1, wherein a small pocket is sealed to the inside of the pouch walls and contains a deodorant therein such as charcoal. A small perforation permits gas to escape through the pocket. Such a device, in being located in the sidewall, has the disadvantage of permitting fluid material from the ostomy drainage pouch to escape therefrom. Moreover, a small total surface area of the deodorant is expose to the gas within the pouch and generally does not effectively eliminate the odor.

SUMMARY OF THE INVENTION

This invention provides a deodorant in association with an aperture located in an uppermost portion of an ostomy draining receptacle for removing offensive odors therefrom upon egress of the gas from the receptacle.

According to this invention, the receptacle comprises a flexible pouch defined by flat, flexible plastic walls sealed at their peripheries. The walls can be formed as double walls to provide a completely sealed air space between the inner and outer walls of the pouch to extend the useful life of the pouch without sacrificing comfort. An opening is provided through one of said walls or double walls adjacent to an upper portion of the pouch and a mounting assembly surrounds the opening for receiving the stoma. An aperture also exists in the upper portion of the pouch in association with a deodorant for abating odorous gas egression.

According to another aspect of this invention, the deodorant is contained in a bag which can be heat or ultrasonically sealed to the uppermost portion of the flexible pouch. The bag contains any conventional deodorant such as activated charcoal and has perforations or openings therein to permit the gas in the flexible pouch to pass through the deodorant and out of the pouch through the aperture.

According to a still further aspect of this invention, the deodorant is generally in the form of a solid such as granules or a block. An effective deodorizing ostomy flexible pouch receptacle is thus provided.

A desirable aspect of this invention is that the deodorant containing bag tends to separate the upper walls of the pouch to accommodate the protruding stoma and minimize chafing of the stoma by the opposite pouch wall.

DETAILED DESCRIPTION OF THE INVENTION

Figure 1:
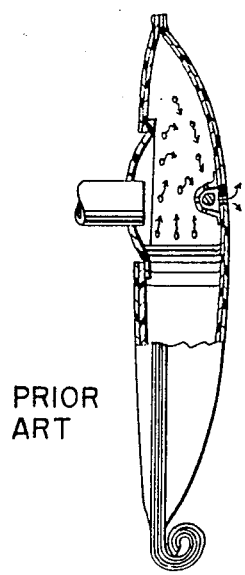
FIG. 1 is a cross-sectional view of the upper portion of an ostomy drainage receptacle of a prior art device.

Referring now to the drawings, an ostomy drainage receptacle generally indicated by the numeral 10 is formed by a front wall 12 and a rear wall 14 which define a drainage chamber 16. The walls 12 and 14 are generally formed from conventional materials, desirably thermoplastics such as polyethylene, polyester, nylon, and the like, and have a suitable wall thickness or, alternatively, can be formed from double walls as set forth in U.S. Pat. No. 3,385,298. The walls 12 and 14 are heat-sealed about their peripheries to form a leakproof seal as well as to define the chamber 16.

A drainage opening 20 exists at the bottom of the chamber and in such a location the walls 12 and 14 are not sealed. The drainage opening 20, which is desirably located at the lowermost portion of the chamber, can be sealed by a suitable clip (not shown) during usage such as set forth in U.S. Pat. No. 4,460,359. Thus, the flexible pouch can be emptied whenever desired by removing the clip and permitting the contents to be drained therefrom.

Figure 2:
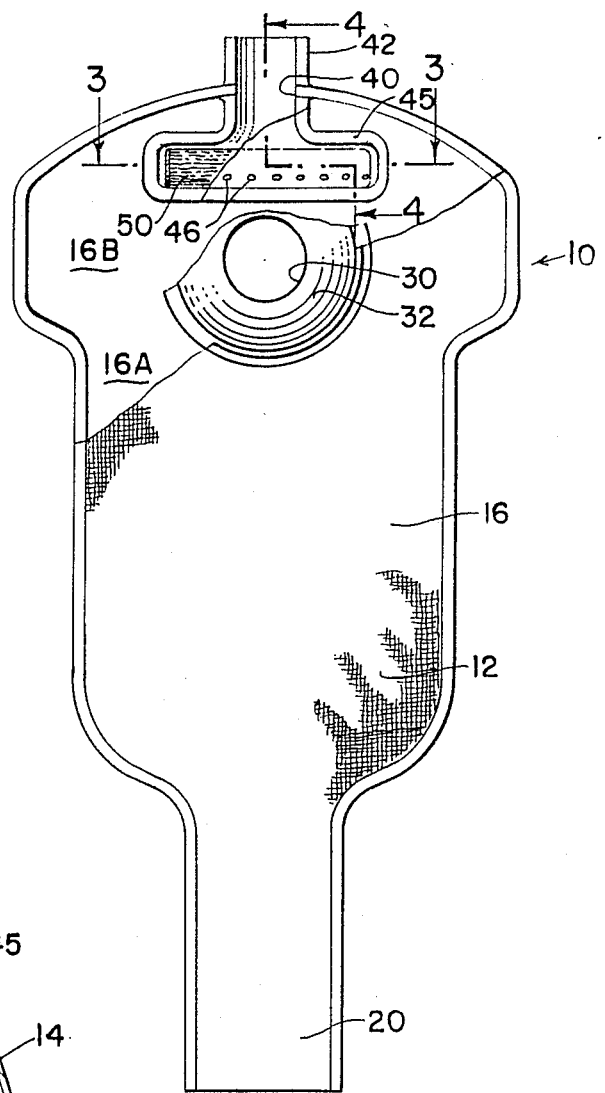
FIG. 2 is a side-elevational view of the deodorizing ostomy receptacle of the present invention illustrating the use of a deodorant in the upper portion of the receptacle with portions of the drawing broken away for clarity.
Figure 4:
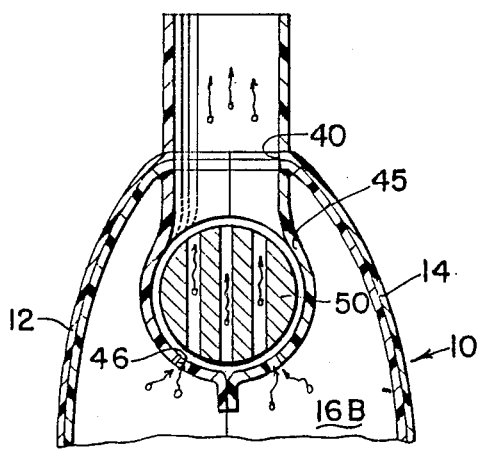
FIG. 4 is a cross-sectional view taken on lines 4-4 of FIG. 2.
Figure 3:
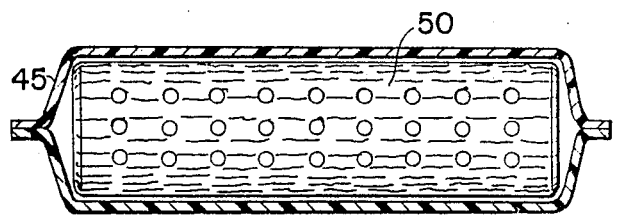
FIG. 3 is a cross-sectional view of the deodorant contained in a bag.

The flexible pouch or drainage receptacle 10 can be attached to an individual's body in any conventional manner as known to the art and to the literature, for example as through the use of an adhesive (not shown), a belt (not shown), and the like. The pouch or drainage receptacle 10 can generally be of any size, shape, or configuration. In the particular embodiment shown, the flexible pouch has a smaller, lower chamber 16A, and a larger upper chamber 16B. As apparent from FIG. 2, the upper chamber has a wall opening 30. Amounting assembly 32 is provided in the opening to surround a stoma (not shown). The mounting assembly can be of any conventional design or structure known to the art and to the literature. An important aspect of the mounting assembly is that it is designed to conveniently receive and retain a stoma from an individual so that gas, liquid, and solid materials are collected. A problem associated with ostomy drainage receptacles or pouches is the generally unpleasant odor associated therewith. It is with regard to such odor that the aspects of the present invention are generally directed.

An aperture 40 is generally located in the upper portion of the flexible pouch and preferably in the uppermost vicinity or portion of the upper drainage chamber 16B. The aperture acts as a vent and permits gas to freely pass out of the drainage receptacle, that is, the flexible pouch. The aperture is, thus, preferably located above the wall opening 30. This location ensures that the aperture is essentially free from emitting any liquid and/or solid material accumulated within the flexible pouch. The provision of the deodorant bag 45 being located in the uppermost vicinity of the drainage chamber further ensures that it will not become plugged or fouled by intestine emitted material. An optional aspect of the present invention relates to the fact that a tube 42, for example made of a thermoplastic material can surround the exterior portion of the aperture and extend upwardly therefrom so that it can be closed as through the utilization of a clip.

A deodorant containing bag 45 is applied to the vicinity of the aperture an internally surrounds the entire aperture so that any gas egressing from the flexible pouch must pass through the bag. The bag 45 can be applied about the aperture in any conventional manner as by heat sealing the bag thereto, by the application of ultrasonic waves, and the like. The bag is thus generally attached to the front wall 12 as well as to the back wall 14. The bag typically has a plurality of perforations therein and can be of any size and shape to accommodate a deodorant. Naturally, the perforations are of a size to allow a gas to pass into the bag and yet retain the deodorant therein.

A deodorant 50 is generally a solid and can exist in any size or shape as for example granule, pellet, or block form. The block form generally is porous or may have holes, that is apertures, extending entirely therethrough. Various conventional materials can be utilized as the deodorant as well as materials known to the art and to the literature. A preferred deodorant is activated charcoal.

In order to deodorize the gas contained in the flexible pouch, it is desirable that the gas generally flow through the deodorant. That is, the gas must substantially or preferably pass through the deodorant before egressing through the aperture 40. Regardless of the shape of the deodorant, for example a solid block, particles, granules, or the like, the perforations 46 are thus located such that the gas, upon being admitted to the deodorizing bag 45, must generally pass through the deodorant before egressing from the bag. When a solid block is utilized, the sides of the bag 45 desirably engage the sides of the activated charcoal deodorant block 50 about the entire perimeter thereof in a gas tight engagement to prevent the gas from by-passing the deodorant. The perforations 46 are thus located in the bottom of the bag and communicate with the upper drainage chamber 16B. Gas in the flexible bag will thus pass through the bag perforations 46, through the activated charcoal where it is abated, substantially reduced, or eliminated, and then through the aperture 40 whereby it is vented to the atmosphere.

The deodorant bag can generally be of any size or shape. Desirably, the bag is elliptical, such as in the shape of a pear or an egg with the deodorant being located in the wider, bottom portion thereof. An advantage of locating the bag in the upper portion of the flexible pouch is that it maintains the top of the pouch walls, that is the front wall 12 and the rear wall 14, separate from each other. Such separation is generally effective in preventing the pouch from collapsing upon itself and causing chafing or irritation to the protruding stoma. Another advantage is that the upper portion of the pouch is generally wider than the lower portion and thus provides room for a stoma to extend into the same.

The embodiment and structure of the present invention thus permits efficient deodorizing of substantially all of the gas egressing from the flexible pouch as well as minimizing any escape of liquid or solid matter from the draining receptacle.

Although the preferred embodiment of the invention has been shown and described, it is to be understood that various modifications and rearrangements of the parts can be resorted to without departing from the scope of the invention as disclosed and claimed herein.

What is claimed is:

1. A deodorizing ostomy pouch comprising a flexible pouch having drainage chamber defining walls, a means defining an opening in one of said walls, said opening means located in an upper portion of said pouch, said opening means capable of receiving a stoma, an aperture permitting gas in said pouch to egress therefrom, said aperture located in the uppermost portion of said pouch, and a bag containing a deodorant therein being attached to said pouch in the vicinity of said aperture, said bag having at least one perforation therein communicating with the interior of the flexible pouch, said bag preventing said walls of said flexible pouch from collapsing upon themselves, said deodorant being located in said bag between said perforation and said aperture, said bag being defined by a pair of walls which are spaced from and facing said drainage chamber defining walls, and each of which is provided with a plurality of perforations therethrough.

2. A deodorizing ostomy pouch according to claim 1, wherein said deodorant bag is attached to said pouch entirely about said aperture.

3. A deodorizing ostomy pouch according to claim 2, wherein said aperture is located in said flexible pouch at a position relatively above said opening means.

4. A deodorizing ostomy pouch according to claim 1, wherein said deodorant is activated charcoal.

5. A deodorizing ostomy pouch comprising a flexible pouch having a front wall and a back wall defining drainage chamber, a means defining an opening in one of said walls, said opening means located in an upper portion of said pouch, said upper portion of said pouch being wider than the remaining portion of said pouch, said opening means capable of receiving a stoma, an aperture permitting gas in said pouch to egress therefrom, said aperture located in an upper portion of said pouch, a bag containing a deodorant therein attached to both said front wall and said back wall so that the gas in said pouch must substantially pass through said deodorant before egressing through said aperture, and a tube exteriorly surrounding said aperture and extending upwardly therefrom, said bag being defined by a pair of side walls which are spaced from and facing said drainage chamber defining walls, and each of which is provided with a plurality of perforations therethrough.

6. A deodorizing ostomy pouch according to claim 5, wherein said deodorant is activated charcoal.

* * * * *

UNITED STATES PATENT AND TRADEMARK OFFICE
CERTIFICATE OF CORRECTION

PATENT NO. :   4,911,699

DATED      :   March 27, 1990

INVENTOR(S) :  Leonard Fenton

It is certified that error appears in the above-identified patent and that said Letters Patent is hereby corrected as shown below:

Column 1, Line 5, "Nov." should read --March--.

Column 1, Line 36, "expose" should read --exposed--.

Column 2, Line 32, "Well" should read --well--.

Column 3, Line 14, "an" should read --and--.

Signed and Sealed this

Twenty-third Day of July, 1991

Attest:

HARRY F. MANBECK, JR.

Attesting Officer

Commissioner of Patents and Trademarks